United States Patent
Friedlander et al.

(10) Patent No.: US 10,331,626 B2
(45) Date of Patent: Jun. 25, 2019

(54) MINIMIZATION OF SURPRISAL DATA THROUGH APPLICATION OF HIERARCHY FILTER PATTERN

(71) Applicant: International Business Machines Corporation, Armonk, NY (US)

(72) Inventors: Robert R. Friedlander, Southbury, CT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 657 days.

(21) Appl. No.: 14/476,234

(22) Filed: Sep. 3, 2014

(65) Prior Publication Data
US 2015/0095293 A1  Apr. 2, 2015

Related U.S. Application Data

(63) Continuation of application No. 13/491,884, filed on Jun. 8, 2012, which is a continuation-in-part of
(Continued)

(51) Int. Cl.
*G06F 19/22*  (2011.01)
*G06F 16/174*  (2019.01)
(Continued)

(52) U.S. Cl.
CPC .... *G06F 16/1744* (2019.01); *G06F 16/24578* (2019.01); *G16B 30/00* (2019.02); *G16B 50/00* (2019.02)

(58) Field of Classification Search
CPC .......... G06F 19/10; G06F 19/22; G06F 19/28; G06F 19/18; G06F 19/24;
(Continued)

(56) References Cited

U.S. PATENT DOCUMENTS 6,401,043 B1  6/2002  Stanton, Jr.
6,468,744 B1  10/2002  Cronin
(Continued)

FOREIGN PATENT DOCUMENTS

CN  101430742 A  5/2009
CN  102081707 A  6/2011
(Continued)

OTHER PUBLICATIONS

Definition of DNA ScienceDaily.com downloaded 2018.*
(Continued)

*Primary Examiner* — Mary K Zeman
(74) *Attorney, Agent, or Firm* — Brown & Michaels, PC; Jay Wahlquist

(57) ABSTRACT

A computer product and system of minimizing surprisal data comprising: at a source, reading and identifying characteristics of an organism's background associated with a genetic sequence of the organism; receiving an input of rank of at least two identified characteristics of the genetic sequence; generating a hierarchy of ranked, identified characteristics based on the rank of the identified characteristics; comparing the hierarchy of ranked, identified characteristics to a repository of reference genomes; and if at least one reference genome from the repository matches the ranked characteristics, breaking the matched reference genomes into pieces, combining pieces associated with the identified characteristics from the matched reference genome to form a filter pattern to be compared to the nucleotides of the genetic sequence of the organism. The differences from the comparison are used to create surprisal data representing an entire genome of the organism.

13 Claims, 5 Drawing Sheets

Related U.S. Application Data application No. 13/475,183, filed on May 18, 2012, now Pat. No. 8,855,938.

(51) Int. Cl.
  *G06F 16/2457*  (2019.01)
  *G16B 30/00*  (2019.01)
  *G16B 50/00*  (2019.01)

(58) Field of Classification Search
  CPC .. G06F 2209/484; G06F 9/52; G06F 16/1744; G06F 12/0877; G06F 12/1408; G06F 16/13; G06F 16/9024; G06F 19/14; G06F 19/26; G06F 19/70; G06F 21/6245; G06F 2212/1052; G06F 2212/6042; G06F 16/137; G06F 16/24578; G06F 16/90344; G06F 17/30985; G06F 19/12; G06F 19/321; G06F 3/0608; G06F 3/0647; G06F 3/0661; G06F 3/0673; G06F 16/2228; G06F 16/2365; G06F 16/2455; G06F 16/24575; G06F 16/284; G06F 16/285; G06F 17/30153; G06F 17/30321; G06F 17/3053; G06F 19/00; G06F 19/3418; G06F 19/3431; G06F 21/62; G06F 21/6254; G06F 21/76; G06F 2221/2107; H04L 45/00; H04L 67/10; H04L 2209/88; H04L 63/0435; H04L 65/607; H04L 67/12; H04L 69/04; H04L 9/008; H04L 9/0618; H04L 2209/30; H04L 2209/34; H04L 63/0428; H04L 63/0471; H04L 9/0861; H04L 9/0869; H04L 9/0894; H04L 9/12; H04L 9/14; H04L 9/3231; G06N 7/005; G06N 3/002; G06N 10/00; H03M 7/30; H03M 7/3068; H03M 7/40; H03M 13/00; H03M 7/3088; H03M 7/3093; H03M 7/42; H03M 7/70; G06K 9/6269; G06K 9/6297; G16H 10/60; G16H 30/20; G16H 50/30; G16B 30/00; G16B 50/00; G16C 99/00
  See application file for complete search history.

(56) References Cited

U.S. PATENT DOCUMENTS

| | | | |
|---|---|---|---|
| 6,609,085 B1 | 8/2003 | Uemura et al. | |
| 7,017,186 B2 | 3/2006 | Day | |
| 8,012,740 B2 | 9/2011 | Hillis | |
| 8,055,063 B2 | 11/2011 | Angell | |
| 8,078,407 B1 | 12/2011 | Brown | |
| 8,126,655 B2 | 2/2012 | Katoh et al. | |
| 8,145,582 B2 | 3/2012 | Angell | |
| 8,296,268 B2 | 10/2012 | Ingles | |
| 8,340,914 B2 * | 12/2012 | Gatewood | H03M 7/3084 702/19 |
| 8,751,166 B2 | 6/2014 | Friedlander et al. | |
| 8,812,243 B2 | 8/2014 | Cardonha et al. | |
| 8,855,938 B2 | 10/2014 | Friedlander et al. | |
| 2003/0100999 A1 | 5/2003 | Markowitz | |
| 2003/0194711 A1 | 10/2003 | Zapala | |
| 2003/0195706 A1 | 10/2003 | Korenberg | |
| 2003/0220844 A1 | 11/2003 | Marnellos | |
| 2003/0233197 A1 | 12/2003 | Padilla et al. | |
| 2004/0153255 A1 | 8/2004 | Ahn | |
| 2004/0224334 A1 | 11/2004 | Shibuya | |
| 2005/0019787 A1 | 1/2005 | Berno | |
| 2005/0267693 A1 | 12/2005 | Allard | |
| 2006/0020398 A1 | 1/2006 | Vernon et al. | |
| 2006/0112264 A1 | 5/2006 | Agarwal | |
| 2006/0166224 A1 | 7/2006 | Norviel | |
| 2007/0105792 A1 | 5/2007 | DiMartino | |
| 2007/0276610 A1 | 11/2007 | Korenberg | |
| 2007/0282538 A1 | 12/2007 | Narasimhan et al. | |
| 2008/0077607 A1 | 3/2008 | Gatawood et al. | |
| 2008/0154512 A1 | 6/2008 | Leong | |
| 2008/0294692 A1 | 11/2008 | Angell et al. | |
| 2009/0006002 A1 | 1/2009 | Honisch | |
| 2009/0018994 A1 | 1/2009 | Hajdukiewicz | |
| 2009/0158211 A1 | 6/2009 | Gogolak | |
| 2009/0182862 A1 | 7/2009 | Thomson | |
| 2010/0113299 A1 | 5/2010 | Von Hoff et al. | |
| 2010/0241670 A1 | 9/2010 | Justice | |
| 2011/0029341 A1 | 2/2011 | Muse et al. | |
| 2011/0087436 A1 | 4/2011 | Klapa | |
| 2011/0213212 A1 | 9/2011 | Al-Ali | |
| 2011/0319298 A1 | 12/2011 | Benner | |
| 2012/0066001 A1 | 3/2012 | Sanborn | |
| 2012/0185612 A1 | 7/2012 | Zhang et al. | |
| 2012/0197533 A1 | 8/2012 | Nazarenko | |
| 2012/0230326 A1 | 9/2012 | Ganeshalingam | |
| 2012/0278362 A1 | 11/2012 | Mande et al. | |
| 2013/0024435 A1 | 1/2013 | Poirier et al. | |
| 2013/0262465 A1 | 10/2013 | Galle et al. | |

FOREIGN PATENT DOCUMENTS

| | | | |
|---|---|---|---|
| CN | 102222174 A | 10/2011 | |
| JP | 2004240975 | 8/2004 | |
| WO | 2063479 A1 | 8/2002 | |
| WO | 3081509 A2 | 10/2003 | |
| WO | 3083442 A2 | 10/2003 | |
| WO | 2005107412 A2 | 11/2005 | |
| WO | 2010072382 A1 | 7/2010 | |
| WO | 2011076130 A1 | 6/2011 | |
| WO | WO 2011076130 A1 * | 6/2011 | ............. G06F 19/22 |

OTHER PUBLICATIONS

Definition of DNA, wikipedia.org downloaded 2018.*
Definition of RNA wikipedia.org downloaded 2018.*
Cao et al. 2010 BMC Bioinformatics 11: 599 pp. 1-16. 2010; PTO-1449.*
Ernst, J. and Bar-Joseph, Z. "STEM: a tool for the analysis of short time series gene expression data." BMC Bioinformatics, 7:191, Apr. 2006.
Ernst, J. et al. "Clustering Short Time Series Gene Expression Data." Bioinformatics, 21 Suppl. 1, pp. i159-i168, Mar. 2005.
Abe, Hidenao et al., "Implementing an Integrated Time-Series Data Mining Environment Based on Temporal Pattern Extraction Methods: A Case Study of Interferon Therapy Risk Mining for Chronic Hepatitis," 2006, Springer Berlin Heidelberg, New Frontiers in Artificial Intelligence, Lecture Notes in Computer Science, vol. 4012, pp. 425-435.
SsahaSNP: Sequence Search and Alignment by Hashing Algorithm; http://www.sanger.ac.uk/resources/software/ssahashp/; Wellcome Trust Sanger Institute; 2011; 2 pages.
He, Q. et al; A Variable Selection Method for Genome-wide Association Studies; Dept. of Biostatistics, Univ. of North Carolina; Oct. 2010; pp. 1-8.
GWASelect: A Variable Selection Method for Genomewide Association Studies ; http://www.bios.unc.edu/~lin/software/GWASelect; at least as early as Feb. 23, 2010; 1 page.
Ruschendorf, F. et al.; "ALOHOMORA: a tool for linkage analysis using 10K SNP Array Data"; BioInformatics Applications Note; vol. 21, No. 9, 2005; pp. 2123-2125.
Hoffmann K. et al.; "easyLINKAGE-Plus—automated linkage analyses using large-scale SNP data"; BioInformatics Applications Note, vol. 21 No. 17 2005. pp. 3565-3567.
International HapMap Project; http://hapmap.ncbi.nlm.nih.gov/cgi-perl/gbrowse/hapmap27_B36/; Feb. 2009; 2 pages.
International HapMap Project: http://en.wikipedia.org/wiki/International_HapMap_Project; Oct. 27, 2002; 4 pages.
Jorde, L. B. et al.; Genetic variation, classification and 'race'; 2004; Nature Genetics 36 (11 Suppl): S28-S33; 8 pages.
Tishkoff, S. A. et al., Implications of biogeography of human populations for 'race' and medicine; Nature Genetics 36 (11 Suppl): S21-7; 2004; 9 pages.

(56) References Cited

OTHER PUBLICATIONS

International HapMap Project; http://hapmap.ncbi.nlm.nih.gov/; 2009; 3 pages.
Human Genome Project Information; http://www.ornl.gov/sci/techresources/Human_Genome/fag/fags1.shtml; 1990; 9 pages.
Wacker, S.A. et al; Using transcriptome sequencing to identify mechanisms of drug action and resistance; Nature Chemical Biology; Feb. 2012; 37 pages.
Brandon, M.G. et al., "Data structures and compression algorithms for genomic sequence data"; BioInformatics—vol. 25: 2009; pp. 1731-1738.
Cao, M.D. et al.: "Agenome alignment algorithm based on compression"; BMC Cioinformatics; 2010; 16 pages.
Christley, S. et al., "Human genomes as email attachments"; Bio Informatics—vol. 25; 2009; pp. 274-275.
Human Genome Diversity Project; http://wikipedia.org/wiki/Human_Genome_Diversity_ Project; 2012; 5 pages.
Cavalli-Sforza, L., "The Human Genome Diversity Project: past, present and future";Nature Reviews/Genetics; Apr. 2005; 8 pages.
Rosenberg, N.A.; "Standardized subsets of the HGDP-CEPH Human Genome Diversity Cell LIne Panel, accounting for atypical and duplicated samples and pairs of close relatives"; Annals of Human Genetics; Feb. 2006; 40 pages.
Amigo, J. et al.; SPSmart: adapting population based SNP genotype databases for fast and comprehensive web access; BMC Bioinformatics; Oct. 2008; 6 pages.
Li, J.A. et al; "Worldwide Human Relationships Inferred from Genome-Wide Patterns of Variation"; Science—vol. 319; 2008; 6 pages.
Novembre, J. et al., "Genes mirror geography within Europe"; Nature; Nov. 2008; 13 pages.
Grumbach, S. et al.; A New Challenge for Compression Algorithms: Genetic Sequences; Genetic Sequences; 1994;12 pages.
International PCT Search Report for PCT/IB2013/052011; dated Jun. 18, 2013; 8 pages.
PCT Search Report for PCT/IB2013/052012 dated Aug. 15, 2013; 10 pages.
Craig et al. "Ordering of cosmid clones covering the Herpes simplex virus type I (HSV-1) genome: a test case for fingerprintingby hybridisation." Nucleic Acids Research, vol. 18, No. 9, pp. 2653-2660. 1990.
Hillman-Jackson, J. et al; "Using Galaxy to Perform Large-Scale Interactive Data Analyses"; Current Protocols in Bioinformatics, Jun. 2012; 47 pages.
Galaxy Wiki; http://wiki.g2.bx.psu.edu/; At least as early as 2011; 2 pages.
Galaxy Wiki; "Custom Genomes"; http://wiki.g2.bx.psu.edu/Learn/CustomGenomes; At least as early as Apr. 2012; 4 pages.
Galaxy—Rous; "Comparing genomic intervals using galaxy"; http://rous.mit.edu/index.php/Comparing_genomic_intervals_using_galaxy; At least as early as Jan. 27, 2010; 2 pages.
The Galaxy Team; "An Introduction to Galaxy"; http://UseGalaxy.org; Jul. 28, 2011; 107 pages.
"Christopher Schmid;""Reviews in Computational Biology Comparing Epigenetic Maps: Computational tasks andaspects of data analysis"""; Swiss Tropical and Public Health Institute; May 2, 2011; 31 pages."
Centroid definition , "The Penguin Dictionary of Mathematics" 2008.
Kohane, I et al.; "Health Information Identification and De-Identification Toolkit"; Proc AMIA Symp.; 1998; pp. 356-360.
Malin, B.; "An Evaluation of the Current State of Genomic Data Privacy Protection Technology and a Roadmap for the Future"; J Am Med Inform Assoc.; Dec. 2005; pp. 28-34.
Kapis, K. et al.; "Security Mechanisms for Electronic Patient Records in Mobile Intelligent Services"; MEDINF; Craiova Medicala Journal; Oct. 2003; 4 Pages.
Heurix, J. et al.; "A Hybrid Approach Integrating Encryption and Pseudonymization for Protecting Electronic Health Records"; Proceedings of the Eighth IASTED International Conference on Biomedical Engineering; 2011; 8 pages.
Weerasinghe, D. et al.; "Securing electronic health records with novel mobile encryption schemes"; Int. J. Electronic Healthcare; 2007, vol. 3 No. 4; pp. 395-416.
Dean, J. et al; MapReduce: Simplified Data Processing on Large Clusters; OSDI; 2004; pp. 1-13.
Hedlund, B.; Understanding Hadoop Clusters and the Network; http://bradhedlund.com/?p=3108; Sep. 10, 2011; 26 pages.
Titmus, M. et al.; Answering the demands of digital genomics; Concurrency and Computation: Practice and Experience; Aug. 2012; 12 pages.
Schadt, E. et al.; Computational solutions to large-scale data management and analysis; Nat. Rev. Genet; Sep. 2010; 22 pages.
Shvachko, K. et al.; The Hadoop Distributed File System; IEEE; 2010: 10 pages.
International PCT Search Report for PCT/IB2013/055173; dated Jan. 2, 2014; 9 pages.
Haefliger et al. "Four Novel Members of the Connexin Family of Gap Junction Proteins." The Journal of Biological Chemistry. vol. 267, 1992, pp. 2057-2064.
List of related applications. Apr. 30, 2014.
U.S. Appl. No. 13/467,292; Notice of Allowance dated Mar. 26, 2014 and Non-Final Rejection dated Sep. 18, 2013.
U.S. Appl. No. 13/563,072; Notice of Allowance dated Oct. 24, 2014.
U.S. Appl. No. 13/537,385; Notice of Allowance dated Nov. 26, 2014 and Non-Final Rejection dated Apr. 29, 2014.
U.S. Appl. No. 13/428,339; Notice of Allowance dated Jan. 30, 2014 and Non-Final Rejection dated Sep. 3, 2013.
U.S. Appl. No. 13/491,884; Non-Final Rejection dated Dec. 22, 2014; Non-Final Rejection dated Jun. 25, 2014; Non-Final Rejection dated Jan. 28, 2014.
U.S. Appl. No. 13/475,183; Notice of Allowance dated May 30, 2014 and Non-Final Rejection dated Feb. 12, 2013.
U.S. Appl. No. 13/562,714; Final Rejection dated May 6, 2014; Non-Final Rejection dated Nov. 15, 2013; Requirement for Restriction/Election dated Aug. 8, 2013.
U.S. Appl. No. 13/557,631; Non-Final Rejection dated Feb. 12, 2015; Final Rejection dated May 5, 2014; Non-Final Rejection dated Nov. 7, 2013; Requirement for Restriction/Election dated Aug. 7, 2013.
U.S. Appl. No. 13/428,146; Non-Final Rejection dated Jan. 26, 2015; Final Rejection dated Dec. 20, 2013; Non-Final Rejection dated Jun. 26, 2013.
U.S. Appl. No. 13/491,884; Final Rejection dated Jun. 9, 2015.
U.S. Appl. No. 13/870,324; Non-Final Rejection dated Jun. 2, 2015.
U.S. Appl. No. 13/557,631; Final Rejection dated Jun. 26, 2015.
U.S. Appl. No. 13/428,146; Non-Final Rejection dated Jun. 25, 2015.
U.S. Appl. No. 13/861,607; Non-Final Rejection dated Jul. 10, 2015.
U.S. Appl. No. 13/770,025; Non-Final Rejection dated Jul. 17, 2015.
Garla, V. et al.; "MU2A—reconciling the genome and transcriptome to determine the effects of base substitutions"; Bioinformatoncs; vol. 27 No. 3; Dec. 2010; pp. 416-418.
Zimin, A. et al.; "Assembly reconciliation"; Bioinformatics; vol. 24 No. 1; Dec. 2007; pp. 42-45.
U.S. Appl. No. 14/078,849; Non-Final Rejection dated Oct. 8, 2015.
U.S. Appl. No. 13/852,852; Final Rejection dated Oct. 20, 2015.
U.S. Appl. No. 13/870,324; Final Rejection dated Oct. 29, 2015.
U.S. Appl. No. 13/852,288; Non-Final Rejection dated May 14, 2015.
U.S. Appl. No. 13/861,607; Final Rejection dated Jan. 25, 2016.
"How to: Find transcript sequences for a gene", retrieved from http://www.ncbi.nlm.nih.gov/guide/howto/find-transcript-gene/, as early as Dec. 2009.
Brandon et al. "Data structures and compression algorithms for genomic sequence data", Bioinformatics 2009; 25 (14): 1731-1738; May 2009.

(56) References Cited

OTHER PUBLICATIONS

U.S. Appl. No. 13/861,607; Final Rejection dated Apr. 10, 2017.

* cited by examiner

Fig. 4

Organism sequence:            ...TAGCAATGA...
                                    ^
                                   485

Reference genome sequence:    ...TAGGTTAGA...
                                    ^
                                   485

Surprisal Data:               location of difference: 485
                              number of different nucleic acid bases: 4
                              actual changed nucleic acid bases: CAAT

Fig. 5

Reference genome sequence:    ...TAGGTTAGA...
                                    ^
                                   485
                                    +
Surprisal Data:               location of difference: 485
                              number of different nucleic acid bases: 4
                              actual changed nucleic acid bases: CAAT Organism's complete genome:   ...TAGCAATGA...
                                    ^
                                   485

MINIMIZATION OF SURPRISAL DATA THROUGH APPLICATION OF HIERARCHY FILTER PATTERN

CROSS-REFERENCE TO RELATED APPLICATIONS

This application is a continuation of copending application Ser. No. 13/491,884 filed Jun. 8, 2012, entitled "MINIMIZATION OF SURPRISAL DATA THROUGH APPLICATION OF HIERARCHY FILTER PATTERN, which is a continuation-in-part patent application of copending application Ser. No. 13/475,183, filed May 18, 2012, entitled "MINIMIZATION OF SURPRISAL DATA THROUGH APPLICATION OF HIERARCHY OF REFERENCE GENOMES". The aforementioned applications are hereby incorporated herein by reference.

BACKGROUND

The present invention relates to minimizing surprisal data generated when compared to a reference genome and more specifically to minimizing surprisal data through application of a hierarchy filter pattern.

DNA gene sequencing of a human, for example, generates about 3 billion ($3 \times 10^9$) nucleotide bases. Currently all 3 billion nucleotide base pairs are transmitted, stored and analyzed, with each base pair typically represented as two bits. The storage of the data associated with the sequencing is significantly large, requiring at least 3 gigabytes of computer data storage space to store the entire genome, which includes only nucleotide sequenced data and no other data or information, such as annotations. If the entire genome includes other information, such as annotations, the genome may require terabytes worth of storage. The movement of the data between institutions, laboratories and research facilities is hindered by the significantly large amount of data, the significant amount of storage necessary to contain the data, and the resources necessary to directly transmit the data. For example, some research facilities can spend upwards of $2 million dollars for transmitting genetic data and sending genetic data that is large, for example terabytes of data, that includes annotations and specifics regarding the genetic sequence or genome. The transfer of a genetic sequence that is very large can take a significant amount of time over a network data processing system.

SUMMARY

According to one embodiment of the present invention, a computer program product for minimizing surprisal data representing an entire genome of an organism for compression and transmission, comprising a source computer having one or more processors and one or more computer-readable memories coupled to the one or more processors. The computer program product comprising: one or more computer-readable storage devices, and program instructions, stored on the one or more storage devices, the program instructions comprising: program instructions to, at a source computer, read and identify characteristics of the organism's medical history and background associated with a genetic sequence of an organism; program instructions to receive an input of rank of at least two identified characteristics associated with the genetic sequence of the organism; program instructions to generate a hierarchy of ranked, identified characteristics based on the rank of the at least two identified characteristics of the genetic sequence of the organism; program instructions to compare the hierarchy of ranked, identified characteristics to a repository of reference genomes; and program instructions to transmit to a destination, a compressed, minimized genome representing an entire genome by sending the surprisal data, an indication of the at least one matched reference genome, and how the reference genome were broken into pieces and not sending sequences of nucleotides that are the same in the genetic sequence of the organism and the at least one matched reference genome. If at least one reference genome from the repository matches the hierarchy of ranked, identified characteristics, program instructions to: store the at least one matched reference genome in a repository; break the at least one matched reference genome into pieces comprising nucleotides of the genetic sequence which comprises at least one gene, at least some of the pieces being associated with the identified characteristics; store the pieces which are associated with the identified characteristics in the repository; combine the stored pieces of the at least one matched reference genome into a filter pattern; compare pieces of the nucleotides of the genetic sequence of the organism which comprises at least one gene which correspond to the stored pieces of the at least one matched reference genome to the nucleotides of the filter pattern of the pieces of the at least one matched reference genome, to find differences where nucleotides of the genetic sequence of the organism which are different from the nucleotides of the at least one matched reference genome; use the differences to create surprisal data representing an entire genome of the organism and storing the surprisal data in the repository, the surprisal data comprising a starting location of the differences within the reference genome, how the reference genomes were broken into pieces, a count of a number of differences at the location within the at least one matched reference genome and the nucleotides from the genetic sequence of the organism which are different from the nucleotides of the reference genome.

According to another embodiment of the present invention, a computer system for minimizing surprisal data representing an entire genome of an organism for compression and transmission. The computer system comprising: a source computer having one or more processors, one or more computer-readable memories coupled to the one or more processors and one or more computer-readable storage devices coupled to the one or more processors, and program instructions, stored on at least one of the one or more storage devices for execution by at least one of the one or more processors via at least one of the one or more memories. The program instructions comprising: program instructions to compare nucleotides of the genetic sequence of the organism to nucleotides from a reference genome, to, at a source, read and identify characteristics of the organism's medical history and background associated with a genetic sequence of an organism; program instructions to receive an input of rank of at least two identified characteristics associated with the genetic sequence of the organism; program instructions to generate a hierarchy of ranked, identified characteristics based on the rank of the at least two identified characteristics associated with the genetic sequence of the organism; program instructions to compare the hierarchy of ranked, identified characteristics to a repository of reference genome; and program instructions for transmitting to a destination, a compressed, minimized genome representing an entire genome by sending the surprisal data and the indication of the at least one matched reference genome, and not sending sequences of nucleotides that are the same in the genetic sequence of the organism and the at least one matched reference genome. If at least one reference genome from the repository matches the hierarchy of ranked, identified characteristics, program instructions to: store the at least one matched reference genome in a repository; break the at least one matched reference genome into pieces comprising nucleotides of the genetic sequence which comprises at least one gene, at least some of the pieces being associated with the identified characteristics; store the pieces which are associated with the identified characteristics in the repository; combine the stored pieces of the at least one matched reference genome into a filter pattern; compare pieces of the nucleotides of the genetic sequence of the organism which comprises at least one gene which correspond to the stored pieces of the at least one matched reference genome to the nucleotides of the filter pattern of the pieces of the at least one matched reference genome, to find differences where nucleotides of the genetic sequence of the organism which are different from the nucleotides of the at least one matched reference genome; use the differences to create surprisal data and store the surprisal data in the repository, the surprisal data comprising a starting location of the differences within the reference genome, a count of a number of differences at the location within the at least one matched reference genome, how the reference genomes were broken into pieces and the nucleotides from the genetic sequence of the organism which are different from the nucleotides of the reference genome.

BRIEF DESCRIPTION OF THE SEVERAL VIEWS OF THE DRAWINGS

FIG. 4 shows a schematic of the re-creation of an organism genome sequence using a reference genome and surprisal data.

FIG. 5 shows a schematic overview of a method of data surprisal data reduction of genetic data for transmission, storage, and analysis according to an illustrative embodiment.

DETAILED DESCRIPTION

The illustrative embodiments of the present invention recognize that the difference between the genetic sequence from two humans is about 0.1%, which is one nucleotide difference per 1000 base pairs or approximately 3 million nucleotide differences. The difference may be a single nucleotide polymorphism (SNP) (a DNA sequence variation occurring when a single nucleotide in the genome differs between members of a biological species), or the difference might involve a sequence of several nucleotides. The illustrative embodiments recognize that most SNPs are neutral but some, 3-5%, are functional and influence phenotypic differences between species through alleles. Furthermore, approximately 10 to 30 million SNPs exist in the human population, of which at least 1% are functional. The illustrative embodiments also recognize that with the small amount of differences present between the genetic sequence from two humans, the "common" or "normally expected" sequences of nucleotides can be compressed out or removed to arrive at "surprisal data"-differences of nucleotides which are "unlikely" or "surprising" relative to the common sequences. The dimensionality of the data reduction that occurs by removing the "common" sequences is $10^3$, such that the number of data items and, more importantly, the interaction between nucleotides, is also reduced by a factor of approximately $10^3$—that is, to a total number of nucleotides remaining on the order of $10^3$. The illustrative embodiments also recognize that by identifying what sequences are "common" or provide a "normally expected" value within a genome, and knowing what data is "surprising" or provides an "unexpected value" relative to the normally expected value, the only data needed to re-create the entire genome in a lossless manner is the surprisal data and the reference genome used to obtain the surprisal data. The illustrative embodiment of the present invention also recognizes that specific characteristics of diseases or underlying causes of diseases can and have been attributed to specific genes or nucleotides that are associated with specific reference genomes.

Figure 1:
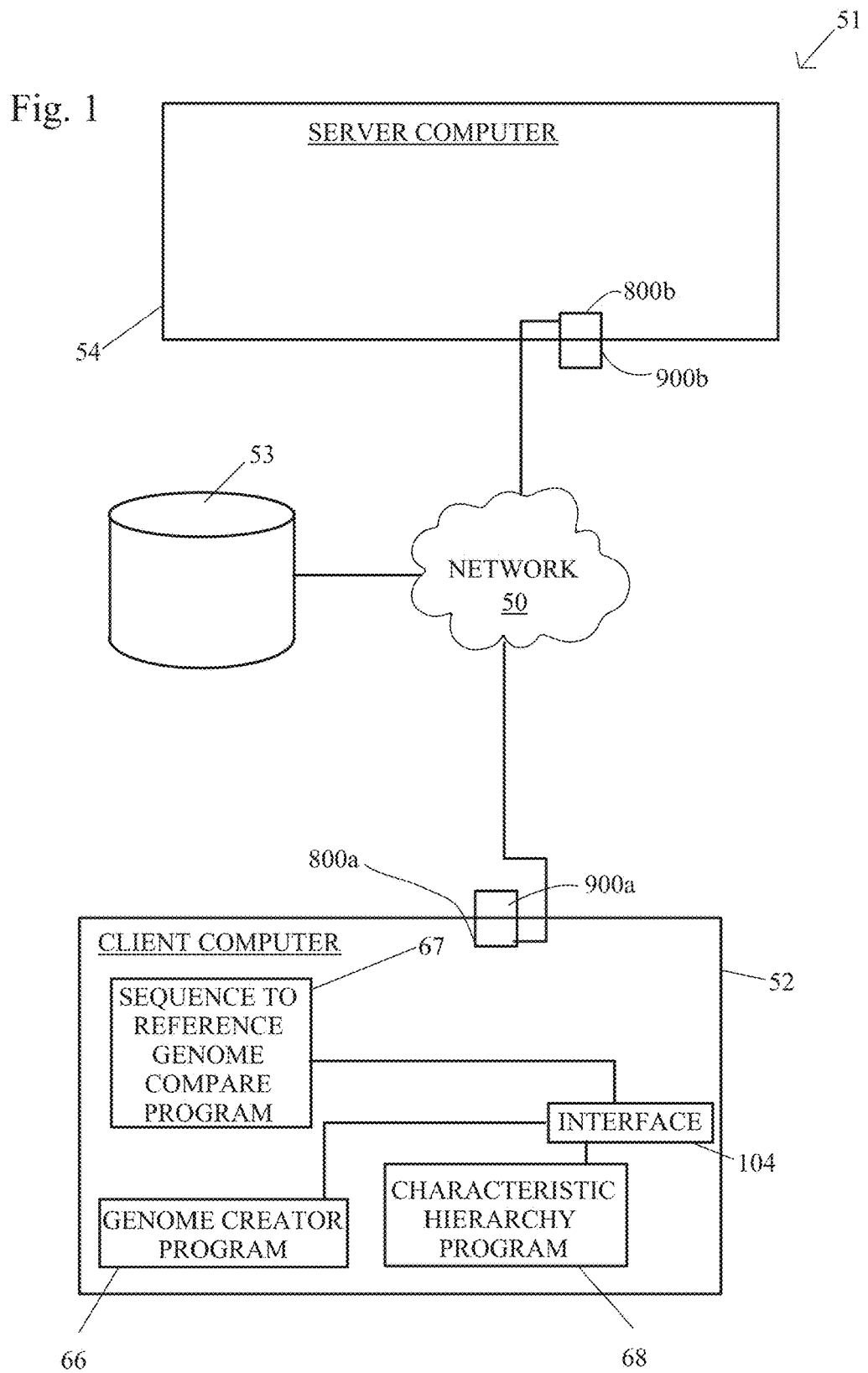
FIG. 1 depicts an exemplary diagram of a possible data processing environment in which illustrative embodiments may be implemented.

FIG. 1 is an exemplary diagram of a possible data processing environment provided in which illustrative embodiments may be implemented. It should be appreciated that FIG. 1 is only exemplary and is not intended to assert or imply any limitation with regard to the environments in which different embodiments may be implemented. Many modifications to the depicted environments may be made.

Referring to FIG. 1, network data processing system 51 is a network of computers in which illustrative embodiments may be implemented. Network data processing system 51 contains network 50, which is the medium used to provide communication links between various devices and computers connected together within network data processing system 51. Network 50 may include connections, such as wire, wireless communication links, or fiber optic cables.

In the depicted example, a client computer 52, server computer 54, and a repository 53 connect to network 50. In other exemplary embodiments, network data processing system 51 may include additional client computers, storage devices, server computers, and other devices not shown. The client computer 52 includes a set of internal components 800a and a set of external components 900a, further illustrated in FIG. 6. The client computer 52 may be, for example, a mobile device, a cell phone, a personal digital assistant, a netbook, a laptop computer, a tablet computer, a desktop computer, a sequencing machine or any other type of computing device.

Client computer 52 may contain an interface 104. The interface can be, for example, a command line interface, a graphical user interface (GUI), or a web user interface (WUI). The interface may be used, for example for viewing an uncompressed sequence from a repository or an entire genome from a repository. The interface may also accept an input regarding a rank of at least two identified characteristics, to display a hierarchy of the inputted identified characteristics that is created, and/or to display matched reference genomes.

In the depicted example, server computer 54 provides information, such as boot files, operating system images, and applications to client computer 52. Server computer 54 can compute the information locally or extract the information from other computers on network 50. Server computer 54 includes a set of internal components 800b and a set of external components 900b illustrated in FIG. 6.

Figure 6:
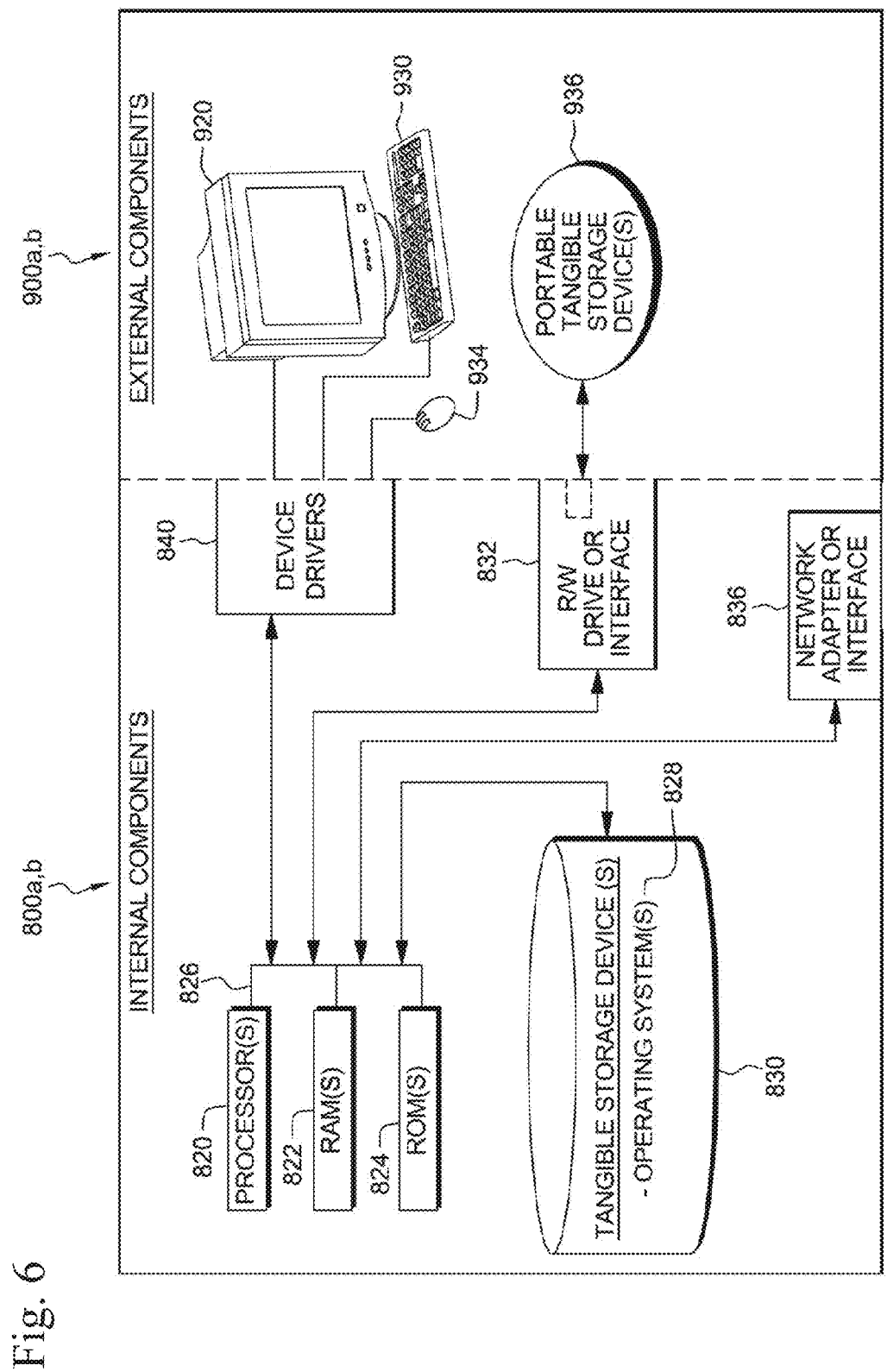
FIG. 6 illustrates internal and external components of a client computer and a server computer in which illustrative embodiments may be implemented.

Program code, reference genomes, and programs such as a sequence to reference genome compare program 67, a genome creator program 66, and/or a characteristic hierarchy program 68 may be stored on at least one of one or more computer-readable tangible storage devices 830 shown in FIG. 6, on at least one of one or more portable computer-readable tangible storage devices 936 as shown in FIG. 6, or repository 53 connected to network 50, or downloaded to a data processing system or other device for use. For example, program code, reference genomes, and programs such as a sequence to reference genome compare program 67, characteristic hierarchy program 68 and/or a genome creator program 66 may be stored on at least one of one or more tangible storage devices 830 on server computer 54 and downloaded to client computer 52 over network 50 for use on client computer 52. Alternatively, server computer 54 can be a web server, and the program code, reference genomes, and programs such as a sequence to reference genome compare program 67, characteristic hierarchy program 68 and/or a genome creator program 66 may be stored on at least one of the one or more tangible storage devices 830 on server computer 54 and accessed on client computer 52. Sequence to reference genome compare program 67, characteristic hierarchy program 68 and/or genome creator program 66 can be accessed on client computer 52 through interface 104. In other exemplary embodiments, the program code, reference genomes, and programs such as sequence to reference genome compare program 67, characteristic hierarchy program 68 and genome creator program 66 may be stored on at least one of one or more computer-readable tangible storage devices 830 on client computer 52 or distributed between two or more servers.

Figure 2:
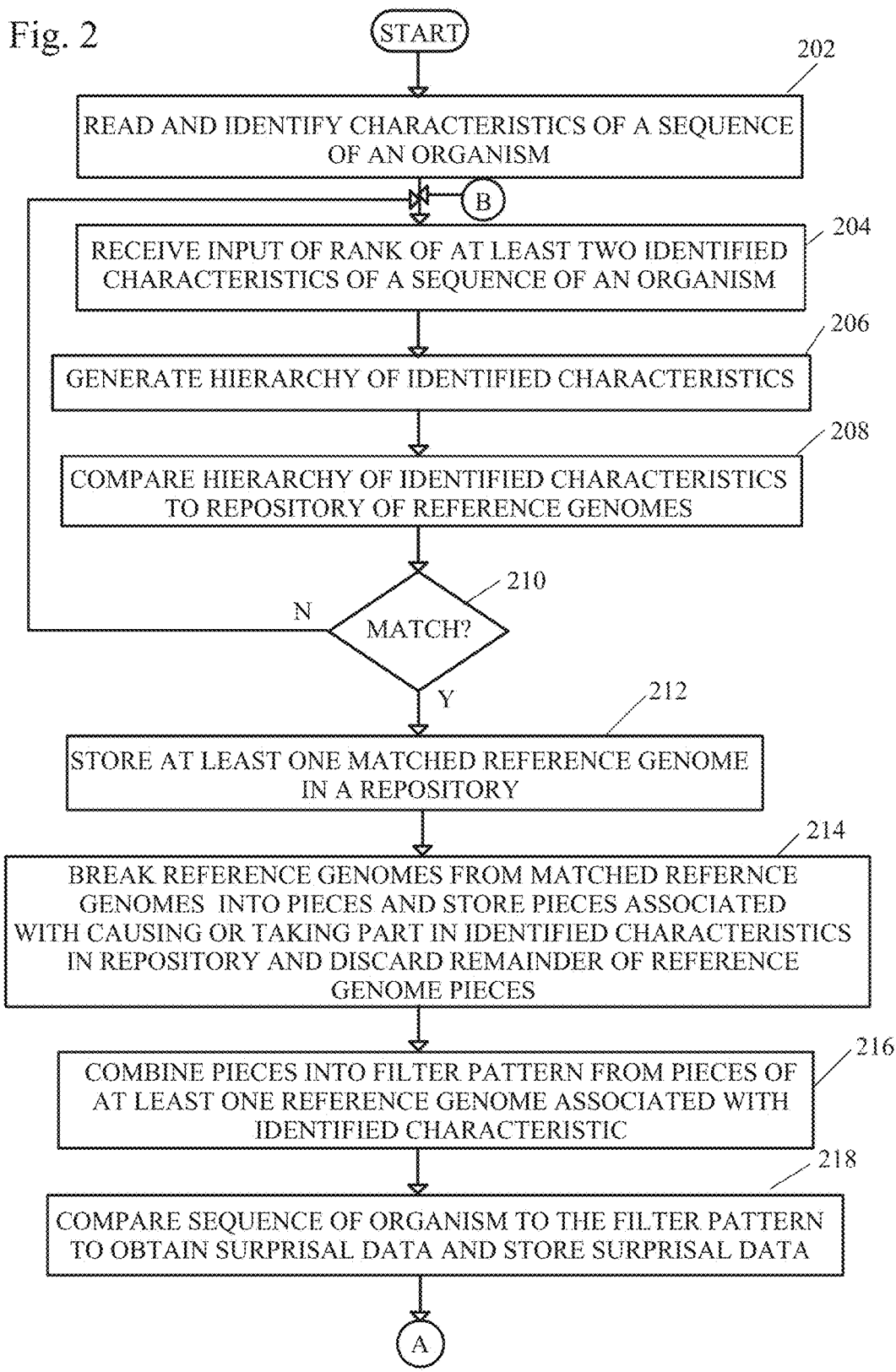
FIG. 2-3 shows a flowchart of a method of minimizing the surprisal data by comparing a sequence to a hierarchy filter pattern.
Figure 3:
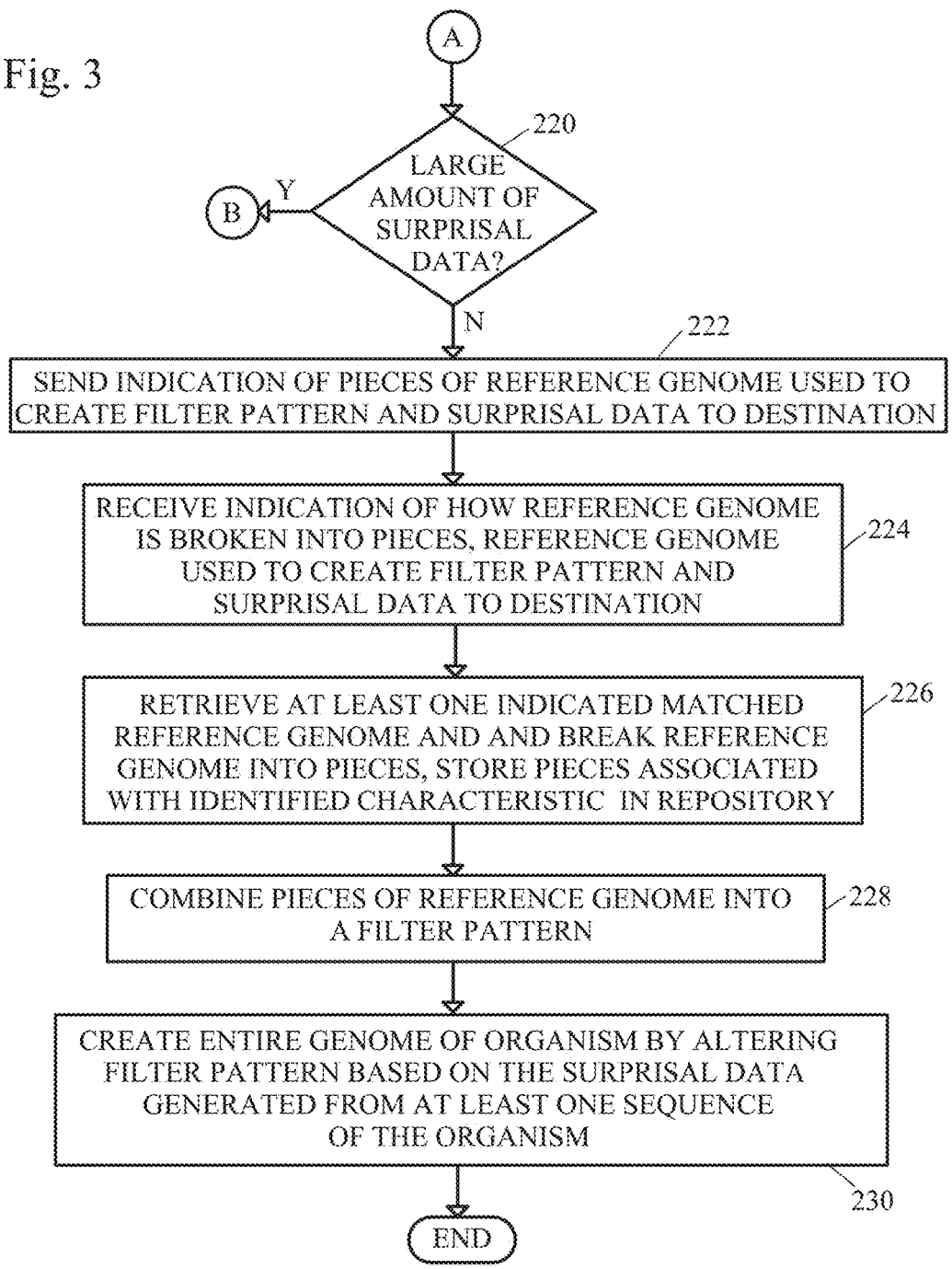

FIGS. 2-3 show a flowchart of a method of minimizing the surprisal data by comparing a sequence to a hierarchy filter pattern.

In a first step, characteristics of at least one genetic sequence of an organism are read and identified from a repository at a source (step 202), for example in repository 53 by the characteristic hierarchy program 68 as shown in FIG. 1. The characteristics may be, but are not limited to, facts regarding a medical history of the organism, demographics of the organism, diagnosed illnesses, and other such characteristics or identifying indicators. The uncompressed genetic sequence of an organism may be a DNA sequence, an RNA sequence, or a nucleotide sequence and may represent a sequence or a genome of an organism. The organism may be a fungus, microorganism, human, animal or plant.

An input of rank of at least two identified characteristics of a sequence of an organism is received from a user (step 204), for example through interface 104. The rank provides the relative value, weight or importance of identified specific characteristics. From the inputted rank of at least two identified characteristics, a hierarchy of identified characteristics is generated (step 206), for example by the characteristic hierarchy program 68.

The hierarchy of identified characteristics generated may be defined as a matter of order, with the order being between the identified characteristics, which are classified in different nested categories, or an ordered series of identified characteristics in which each terms is superior relative to a specific set of identified characteristics. The hierarchy can be: a simple linear hierarchy, a branching network of subcategories, and/or a nested hierarchy of categories.

For example, a hierarchy with a branching network of subcategories may have a primary category of diabetes mellitus and secondary categories of Type 1 [juvenile type] and Type 2 [adult onset]. It should be noted that the two types under the second category are mutually exclusive.

An example of a nested hierarchy of categories may have diabetes mellitus Type 1 [juvenile type] as a primary category and secondary categories of: diabetes with renal manifestations, diabetes with ophthalmic manifestations, diabetes with neurological manifestations, and diabetes with peripheral circulatory disorders. Note that a patient could have from zero to all of the secondary categories. The secondary categories could have additional inclusive or mutually exclusive categories. For example diabetes with neurological manifestations could have Tertiary Categories of: amyotrophy, gastroparalysis, gastroparesis, mononeuropathy, neurogenic arthropathy, peripheral autonomic neuropathy, and/or polyneuropathy.

The hierarchy of identified characteristics is then compared to a repository of reference genomes (step 208). A reference genome is a digital nucleic acid sequence database which includes numerous sequences. The sequences of the reference genome do not represent any one specific individual's genome, but serve as a starting point for broad comparisons across a specific species, since the basic set of genes and genomic regulator regions that control the development and maintenance of the biological structure and processes are all essentially the same within a species. In other words, the reference genome is a representative example of a species' set of genes. As discussed above, specific characteristics of diseases or underlying causes of diseases can and have been attributed to specific genes or nucleotides that are associated with specific reference genomes.

If a match (step 210) is not present between at least one reference genome in the repository and the hierarchy generated of the identified characteristics, then, the method returns to step 204 of receiving an input of the rank of at least two identified characteristics of a sequence of an organism.

The user may set what is considered a match to the hierarchy through the interface, for example interface 104. For example, the user may set that a match between a reference genome and the hierarchy is only present if a match is found with the hierarch or the hierarch and a neighbor, and so on. Alternatively, a match may be based on a probability threshold.

If a match (step 210) is present between at least one reference genome in the repository and the hierarchy generated of the identified characteristics, the at least one matched reference genome is stored in a repository (step 212). The repository may be repository 53 or a separate repository.

The at least one matched reference genome stored in the repository is broken into pieces, some of the pieces being associated with causing or taking part in the identified characteristic. The pieces which are so associated are stored in the repository, and the remainder of the reference genome is discarded (step 214). The pieces may be genes, a series of genes, or pathways.

The stored pieces are combined together to form a filter pattern associated with the identified characteristics of the generated hierarchy (step 216).

The filter pattern of pieces of the matched reference genomes is then compared to the corresponding pieces of a sequence of an organism to obtain surprisal data, and the surprisal data and an indication of the matched reference genome used to prepare the filter pattern is stored in a repository (step 218), for example using a sequence to reference genome compare program 67.

The surprisal data preferably includes how the reference genome was broken into pieces; a location of the difference within the reference genome pieces, the number of nucleic acid bases that are different, and the actual changed nucleic acid bases. Including the number of bases which are different within the surprisal data that is compressed provides a double check of the method by comparing the actual bases to the reference genome bases to confirm that the bases really are different.

FIG. 4 shows a schematic of the comparison of an organism sequence to a piece of a reference genome sequence to obtain surprisal data representing an organism's genome. For example, the surprisal data that resulted from comparing the organism sequence to the reference genome shown in FIG. 4 would be surprisal data consisting of: a difference at location 485 of the reference genome; four nucleic acid base differences relative to the reference genome, and the actual bases present in the sequence at the location, for example CAAT (instead of GTTA).

If a large amount of surprisal data is present from comparing to a sequence of an organism to obtain surprisal data and the surprisal data and an indication of the matched reference genome used to prepare the filter pattern is stored in a repository in step 218, and the method then returns to step 204 of receiving an input of rank of at least two identified characteristics of a sequence of an organism is received from a user. This step is carried out to check to see if the surprisal data is valid. Since the filter pattern is attempting to provide a fine tuned amount of surprisal data and if from comparing the filter pattern to the sequence of a organism, a large amount of surprisal data, then the filter pattern is not specific enough and additional or altered input regarding the hierarchy is necessary.

If a large amount of surprisal data is not present from comparing a sequence of an organism to obtain surprisal data and the surprisal data and an indication of the matched reference genome used to prepare the filter pattern is stored in a repository in step 218, and an indication of how and what reference genomes were broken into pieces and the surprisal data is sent to a destination (step 222). The surprisal data preferably includes a location of the difference within the reference genome pieces, the number of nucleic acid bases that are different, and the actual changed nucleic acid bases. Including the number of bases which are different within the surprisal data that is compressed, provides a double check of the method by comparing the actual bases to the reference genome bases to confirm that the bases really are different.

For example, a user may wish to determine if at least one sequence of an organism yields surprisal data when compared to reference genomes that are associated with type 2 diabetes mellitus, coronary artery disease, but not chronic obstructive pulmonary disease (COPD). A user may therefore assign a rank or weight of 0.6 to the identified characteristic of type 2 diabetes mellitus, a rank or weight of 0.3 to the identified characteristic of coronary artery disease and a rank or weight of 0.1 to COPD.

A reference genome that is associated with type 2 diabetes mellitus and not COPD may be considered a match and would provide a narrowed, filtered amount of surprisal data. Another match could be a reference genome that is associated with coronary disease and not COPD.

The matched reference genomes would then be broken into pieces, for example genes or pathways of genes associated with the insulin production. Another match may be broken into pieces associated with high blood pressure.

A filter pattern is created by combining these pieces of the reference genomes that match. In this example, comparing the sequence of at least one organism to a specific filter pattern from matched reference genomes, maximizes the "common" or "normally expected" sequences of nucleotides that can be compressed out and minimizes the surprisal data, such that the surprisal data that does result from the comparison to both matched reference genomes is increased in relevancy based on the user's input.

The indication of how and what reference genomes were broken into pieces and the surprisal data is received by the destination and stored in a repository (step 224). The indicated reference genomes are then retrieved from a repository and broken into piece as indicated in step 224, for example using a genome creator program 66 and stored in a repository (step 226).

The pieces of the reference genome are then reassembled into the filter pattern that matches the filter pattern used in step 216.

From the surprisal data, the retrieved reference genomes, and the recreated filter pattern, an entire genome of the organism is re-created by finding a location within at least one reference genome that was indicated as having a difference in the surprisal data and alters the bases of the reference genome to be the bases indicated by the surprisal data (step 230), for example by the genome creator program 66. In the example of FIG. 5, based on the surprisal data, a difference is present at location 485, this location is found in the reference genome and GTTA is changed to be CAAT as indicated by the surprisal data.

The surprisal data may be verified by comparing the nucleotides from the genetic sequence of the organism in the surprisal data to the nucleotides in the reference genome at the location. If all of the nucleotides in the surprisal data are different from the nucleotides in the reference genome, the surprisal data is verified. This verification may take place prior to step 222.

Alternatively, the verification may take place simultaneously with step 230 during the creation of the entire genome of an organism by a genome creator program 66. If some of the nucleotides in the surprisal data are the same as the nucleotides in the reference genome, the surprisal data has an error.

It should be noted that in FIGS. 4 and 5, only a portion of both the organism sequence and the reference genome are shown for clarity, and the sequences shown are chosen randomly and do not represent a real DNA sequence of any sort.

FIG. 6 illustrates internal and external components of client computer 52 and server computer 54 in which illustrative embodiments may be implemented. In FIG. 6, client computer 52 and server computer 54 include respective sets of internal components 800a, 800b, and external components 900a, 900b. Each of the sets of internal components 800a, 800b includes one or more processors 820, one or more computer-readable RAMs 822 and one or more computer-readable ROMs 824 on one or more buses 826, and one or more operating systems 828 and one or more computer-readable tangible storage devices 830. The term "tangible storage device" does not encompass a signal propagation media such as a copper cable, optical fiber or wireless transmission media. The one or more operating systems 828, sequence to reference genome compare program 67, characteristic hierarchy program 68 and genome creator program 66 are stored on one or more of the computer-readable tangible storage devices 830 for execution by one or more of the processors 820 via one or more of the RAMs 822 (which typically include cache memory). In the embodiment illustrated in FIG. 6, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

Each set of internal components 800a, 800b also includes a R/W drive or interface 832 to read from and write to one or more portable computer-readable tangible storage devices 936 such as a CD-ROM, DVD, memory stick, magnetic tape, magnetic disk, optical disk or semiconductor storage device. Sequence to reference genome compare program 67, characteristic hierarchy program 68 and genome creator program 66 can be stored on one or more of the portable computer-readable tangible storage devices 936, read via R/W drive or interface 832 and loaded into hard drive 830.

Each set of internal components 800a, 800b also includes a network adapter or interface 836 such as a TCP/IP adapter card. Sequence to reference genome compare program 67, characteristic hierarchy program 68 or genome creator program 66 can be downloaded to client computer 52 and server computer 54 from an external computer via a network (for example, the Internet, a local area network or other, wide area network) and network adapter or interface 836. From the network adapter or interface 836, sequence to reference genome compare program 67, characteristic hierarchy program 68 and genome creator program 66 are loaded into hard drive 830. The network may comprise copper wires, optical fibers, wireless transmission, routers, firewalls, switches, gateway computers and/or edge servers.

Each of the sets of external components 900a, 900b includes a computer display monitor 920, a keyboard 930, and a computer mouse 934. Each of the sets of internal components 800a, 800b also includes device drivers 840 to interface to computer display monitor 920, keyboard 930 and computer mouse 934. The device drivers 840, R/W drive or interface 832 and network adapter or interface 836 comprise hardware and software (stored in storage device 830 and/or ROM 824).

Sequence to reference genome compare program 67, characteristic hierarchy program 68 and genome creator program 66 can be written in various programming languages including low-level, high-level, object-oriented or non object-oriented languages. Alternatively, the functions of a sequence to reference genome compare program 67, characteristic hierarchy program 68 and genome creator program 66 can be implemented in whole or in part by computer circuits and other hardware (not shown).

Based on the foregoing, a computer system, method and program product have been disclosed for minimizing surprisal data. However, numerous modifications and substitutions can be made without deviating from the scope of the present invention. Therefore, the present invention has been disclosed by way of example and not limitation.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A computer program product for minimizing surprisal data representing an entire genome of an organism for compression and transmission, comprising a source computer having one or more processors and one or more computer-readable memories coupled to the one or more processors, comprising:
    one or more computer-readable storage devices, and program instructions, stored on the one or more storage devices, the program instructions comprising:
    program instructions to, at a source computer, read and identify characteristics of the organism's medical history and background associated with a genetic sequence of an organism;
    program instructions to receive an input of rank of at least two identified characteristics of the organism's medical history and background associated with the genetic sequence of the organism;
    program instructions to generate a hierarchy of ranked, identified characteristics based on the rank of the at least two identified characteristics of the genetic sequence of the organism;
    program instructions to compare the hierarchy of ranked, identified characteristics to a repository of reference genomes; and
    program instructions that if at least one reference genome from the repository matches the hierarchy of ranked, identified characteristics, program instructions to:
    i) storing the at least one matched reference genome in a repository;
    ii) breaking the at least one matched reference genome into pieces comprising nucleotides of the genetic sequence which comprises at least one gene, at least some of the pieces being associated with the identified characteristics;
    iii) storing the pieces which are associated with the identified characteristics in the repository;
    iv) combining the stored pieces of the at least one matched reference genome into a filter pattern;
    v) comparing pieces of the nucleotides of the genetic sequence of the organism which comprises at least one gene which correspond to the stored pieces of the at least one matched reference genome to the nucleotides of the filter pattern of the pieces of the at least one matched reference genome, to find differences where nucleotides of the genetic sequence of the organism which are different from the nucleotides of the at least one matched reference genome;
    vi) using the differences to create surprisal data representing an entire genome of the organism and storing the surprisal data in the repository, the surprisal data comprising a starting location of the differences within the reference genome, how the reference genomes were broken into pieces, a count of a number of differences at the location within the at least one matched reference genome and the nucleotides from the genetic sequence of the organism which are different from the nucleotides of the reference genome; and
    vii) transmitting to a destination, a compressed, minimized genome representing an entire genome by sending the surprisal data, an indication of the at least one matched reference genome, and how the reference genome were broken into pieces and not sending sequences of nucleotides that are the same in the genetic sequence of the organism and the at least one matched reference genome.

2. The computer program product of claim 1, further comprising a destination computer having one or more processors and one or more computer-readable memories coupled to the one or more processors performing program instructions to comprising:
    receive the compressed genome from the source computer, the compressed genome comprising surprisal data, the indication of the at least one matched reference genome used to compress the genome, a count of a number of differences at the location within the at least one matched reference genome and how the reference genomes were broken into pieces;
    retrieve the at least one indicated matched reference genome from a repository; and
    break the at least one indicated matched reference genome from the repository into pieces associated with the identified characteristics and storing the pieces associated with the identified characteristic in the repository;
    combine the pieces into the filter pattern;
    alter the filter pattern comprised of pieces of at least one matched reference genome based on the surprisal data by replacing nucleotides at each location in the at least one matched reference genome specified by the surprisal data with the nucleotides from the genetic sequence of the organism in the surprisal data associated with the location; resulting in an entire genome of the organism.

3. The computer program product of claim 1, wherein the organism is an animal.

4. The computer program product of claim 1, wherein the organism is a microorganism.

5. The computer program product of claim 1, wherein the organism is a plant.

6. The computer program product of claim 1, wherein the organism is a human.

7. A computer system for minimizing surprisal data representing an entire genome of an organism for compression and transmission comprising:
a source computer having one or more processors, one or more computer-readable memories coupled to the one or more processors and one or more computer-readable, storage devices coupled to the one or more processors, and program instructions, stored on at least one of the one or more storage devices for execution by at least one of the one or more processors via at least one of the one or more memories, the program instructions comprising:
program instructions to compare nucleotides of the genetic sequence of the organism to nucleotides from a reference genome, to, at a source, read and identify characteristics of the organism's medical history and background associated with a genetic sequence of an organism;
program instructions to receive an input of rank of at least two identified characteristics of the organism's medical history and background associated with the genetic sequence of the organism;
program instructions to generate a hierarchy of ranked, identified characteristics based on the rank of the at least two identified characteristics associated with the genetic sequence of the organism;
program instructions to compare the hierarchy of ranked, identified characteristics to a repository of reference genomes; and
program instructions that if at least one reference genome from the repository matches the hierarchy of ranked, identified characteristics, program instructions to:
  i) storing the at least one matched reference genome in a repository;
  ii) breaking the at least one matched reference genome into pieces comprising nucleotides of the genetic sequence which comprises at least one gene, at least some of the pieces being associated with the identified characteristics;
  iii) storing the pieces which are associated with the identified characteristics in the repository;
  iv) combining the stored pieces of the at least one matched reference genome into a filter pattern;
  v) comparing pieces of the nucleotides of the genetic sequence of the organism which comprises at least one gene which correspond to the stored pieces of the at least one matched reference genome to the nucleotides of the filter pattern of the pieces of the at least one matched reference genome, to find differences where nucleotides of the genetic sequence of the organism which are different from the nucleotides of the at least one matched reference genome;
  vi) using the differences to create surprisal data and store the surprisal data in the repository, the surprisal data comprising a starting location of the differences within the reference genome, a count of a number of differences at the location within the at least one matched reference genome, how the reference genomes were broken into pieces and the nucleotides from the genetic sequence of the organism which are different from the nucleotides of the reference genome; and
  vii) program instructions for transmitting to a destination, a compressed, minimized genome representing an entire genome by sending the surprisal data and the indication of the at least one matched reference genome, and not sending sequences of nucleotides that are the same in the genetic sequence of the organism and the at least one matched reference genome.

8. The system of claim 7, further comprising a destination computer having one or more processors, one or more computer-readable memories coupled to the one or more processors, and one or more storage devices coupled to the one or more processors, and program instructions, stored on at least one of the one or more storage devices for execution by at least one of the one or more processors via at least one of the one or more memories, the program instructions comprising:
program instructions to receive the compressed genome from the source computer, the compressed genome comprising surprisal data, the indication of the at least one matched reference genome used to compress the genome, a count of a number of differences at the location within the at least one matched reference genome and how the reference genomes were broken into pieces;
program instructions to retrieve the at least one indicated matched reference genome from a repository;
program instructions to break the at least one indicated matched reference genome from the repository into pieces associated with the identified characteristics and storing the pieces associated with the identified characteristic in the repository;
program instructions to combine the pieces into the filter pattern; and
program instructions to alter the filter pattern comprised of pieces of at least one matched reference genome based on the surprisal data by replacing nucleotides at each location in the at least one matched reference genome specified by the surprisal data with the nucleotides from the genetic sequence of the organism in the surprisal data associated with the location; resulting in an entire genome of the organism.

9. The system of claim 7, in which the surprisal data further comprises a count of a number of differences at the location within the reference genome.

10. The system of claim 7, wherein the organism is an animal.

11. The system of claim 7, wherein the organism is a microorganism.

12. The system of claim 7, wherein the organism is a plant.

13. The system of claim 7, wherein the organism is a human.

* * * * *